US009035065B2

(12) United States Patent
Balestra et al.

(10) Patent No.: US 9,035,065 B2
(45) Date of Patent: *May 19, 2015

(54) ETHANAMINE COMPOUNDS AND METHODS OF USING THE SAME

(71) Applicant: AstraZeneca AB, Sodertalje (SE)

(72) Inventors: Michael Balestra, Wilmington, DE (US); Peter Bernstein, Wilmington, DE (US); Glen E. Ernst, Wilmington, DE (US); William Frietze, Wilmington, DE (US); John McCauley, Wilmington, DE (US); David Nugiel, Cherry Hill, NJ (US); Lihong Shen, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/748,852

(22) Filed: Jan. 24, 2013

(65) Prior Publication Data

US 2013/0137731 A1    May 30, 2013

Related U.S. Application Data

(63) Continuation of application No. 13/219,892, filed on Aug. 29, 2011, now abandoned, which is a continuation of application No. 12/644,046, filed on Dec. 22, 2009, now Pat. No. 8,013,165.

(60) Provisional application No. 61/140,673, filed on Dec. 24, 2008.

(51) Int. Cl.
| C07D 211/00 | (2006.01) |
| C07D 213/38 | (2006.01) |
| A61K 31/4402 | (2006.01) |
| C07C 57/15 | (2006.01) |

(52) U.S. Cl.
CPC .......... *C07D 213/38* (2013.01); *A61K 31/4402* (2013.01); *C07C 57/15* (2013.01)

(58) Field of Classification Search
USPC .......................................... 546/329; 514/357
See application file for complete search history.

(56) References Cited

U.S. PATENT DOCUMENTS

| 3,422,191 A | 1/1969 | Halpern et al. |
| 5,206,248 A | 4/1993 | Smith |
| 5,455,259 A | 10/1995 | Griffith et al. |
| 5,607,935 A | 3/1997 | Griffith et al. |
| 6,479,553 B1 | 11/2002 | McCarthy |
| 6,518,432 B1 | 2/2003 | Giles |
| 8,013,165 B2 * | 9/2011 | Balestra et al. ............... 546/348 |

FOREIGN PATENT DOCUMENTS

| EP | 0356035 | 2/1990 |
| EP | 0472325 | 2/1992 |
| EP | 0540318 | 5/1993 |
| EP | 0691957 | 8/1997 |
| EP | 0633879 | 3/1998 |
| EP | 0869122 | 10/1998 |
| JP | 50000825 | 1/1975 |
| JP | 50005385 | 3/1975 |
| JP | 2000508672 | 6/2000 |
| JP | 2002539256 | 11/2002 |
| MX | PA01009448 A | 8/2002 |
| WO | WO 93/20052 | 10/1993 |
| WO | WO 94/22831 | 10/1994 |
| WO | WO 99/02497 A2 | 1/1999 |
| WO | WO 00/56324 | 9/2000 |
| WO | WO 2010/074647 A1 | 7/2010 |

OTHER PUBLICATIONS

Berman et al., 'Antidepressant Effects of Ketamine in Depressed Patients', Society of Biological Psychiatry (2000); 47; 4; 351-354.
Blanpied et al., 'Trapping Channel Block of NMDA-activated Responses by Amantadine and Memantine', The Amer. Physiol. Society (1997); 309-323.
Boireau et al., 'The Antidepressant Metapramine is a Low-affinity Antagonist at N-methyl-D-aspartic Acid Receptors', Neuropharmacology (1996); 35; 12; 1703-1707.
Boireau et al., 'The Antidepressant Metapramine is a Low-affinity Antagonist at N-methyl-D-aspartic Receptors', Neuropharmacology (1996); 35; 12; Abstract.
Bolshakov et al., 'Determinants of Trapping Block of N-methyl-D-aspartate Receptor Channels', Journal of Neurochemistry (2003); 87; 56-65.
Brown et al., '2,6-Disubstituted Pyrazines and Related Analogs as NR2B Site Antagonists of the NMDA Receptor with Anti-depressant Activity', Bioorganic & Medicinal Chem Letters (2011); 21; 11; 3399-3403.
Foster et al., 'The Novel Anticonvulsant MK-801 Binds to the Activated State of the N-methyl-D-aspartate Receptor in Rat Brain', Br. J. Pharmac. (1987); 91; 403-409.
Hayes et al., 'Structure-activity Relationship Study of the Inhibition of Adrenal Cortical 11β-Hydroxylase by New Metyrapone Analogues', Journal of Med. Chem (1984); 27; 15-19.
Hudzik et al., 'Remacemide Hydrochloride and ARL 15896AR Lack Abuse Potential: Additional Differences from Other Uncompetitive NMDA Antagonists', Epilepsia (1996); 37; 6; 544-550.
Kodermanski et al., 'Memantine Binding to a Superficial Site on NMDA Receptors Contributes to Partial Trapping', J. Physiol. (2009); 587; 19; 4589-4603.
Krapcho et al., '2-Acylimino-1, 1-dimethylphenethylamines and Related Compounds. Anorectic Agents', Journal of Med. Chem. (1967); 10; 495-497.
Manzano et al., 'Tretinoin Prevents Age-Related Renal Changes and Stimulates Antioxidant Defenses in Cultured Renal Mesangial Cells', J. Pharmacol. and Exper. Therap. (1999); 289; 1; 123-132.

(Continued)

*Primary Examiner* — Nizal Chandrakumar

(57) ABSTRACT

The present invention is directed to ethanamine compounds, pharmaceutical compositions comprising the same, and methods of treating depression by administering the ethanamine compound.

12 Claims, No Drawings

(56) References Cited

OTHER PUBLICATIONS

Mealing et al., 'Structural Modifications to an N-Methyl-D-aspartate Receptor Antagonist Result in Large Differences in Trapping Block', J. Pharmacol. and Exper. Therap. (2001); 297; 3; 906-914.
Office Action issued in U.S. Appl. No. 12/644,046; mailed Mar. 8, 2011.
Oppostion issued against corresponding Chilean Patent Application No. 1590-2011; English description of opposition as provided by Chilean Foreign Counsel; mailed Apr. 8, 2013.
Opposition issued against corresponding Dominican Republic Patent Application No. P2011-0205; mailed Sep. 8, 2011.
Palmer et al., '[S]AR-R 15896AR—A Novel Anticonvulsant: Acute Safety, Pharmacokinetic and Pharmacodynamic Properties', J. Pharmacol. and Exper. Therap. (1999); 288; 121-132.
Palmer et al., 'The Low-Affinity, Use-Dependent NMDA Receptor Antagonist AR-R 15896AR: An Update of Progress in Stroke', Annals New York Academy of Sciences (2006); 406-420.
Peters et al., 'Identification of Short-acting κ-opioid Receptor Antagonists with Anxiolytic-like Activity', Eur. J. Pharmacol. (2011); 661; 1-3; 27-34.
Popoli et al., 'Diphenylhydantoin Potentiates the EEG and Behavioral Effects Induced by N-methyl-D-aspartate Antagonists in Rats', Psychopharmacology (1994); 113; 471-475.
Porter et al., 'Regional Variations in the Pharmacology of NMDA Receptor Channel Blockers: Implications for Therapeutic Potention', Internationl Society for Neurochemistry (1995);64; 2; 614-623.
US Continuation-In-Part U.S. Appl. No. 13/431,303, filed Mar. 27, 2012; now abandoned, and corresponding publication No. is US2012/0279272.
Zarate et al., 'A Randomized Trial of an N-methyl-D-aspartate Antagonist in Treatment-resistance Major Depression', Arch. Gen. Psychiatry (2006); 63; 8; 856-864.
Annex to Communication pursuant to Article 94(3) EPC issued against European application No. 09835355.0; mailed May 30, 2012.
Annex to Communication pursuant to Article 94(3) EPC issued against European application No. 09835355.0; mailed Jun. 4, 2013.
Design of Prodrugs; edited by H. Bundgaard; Elsevier; 1985.
Nielsen et al., 'Glycolamide Esters as Biolabile Prodrugs of Carboxylic Acid Agents: Synthesis, Stability, Bioconversion, and Physicochemical Properties', Journal Of Pharmaceutical Sciences (1988); vol. 77; No. 4; 285-298.
International Written Opinion for International application No. PCT/SE2009/051493; mailed Jun. 29, 2011.
International Search Report for International application No. PCT/SE2009/051493; mailed Jun. 29, 2011.
Communication pursuant to Article 94(3) EPC issued against European application No. 09835355.0; mailed May 30, 2012.
Communication pursuant to Article 94(3) EPC issued against European application No. 09835355.0; mailed Jun. 4, 2013.
Nomenclature of Organic Chemistry; Sections A, B, C, D, E, F, and H; Pergamon Press; Oxford; 1979.
Methods in Enzymology; vol. 42; 309-396; edited by W. Wood et al., Academic Press; 1975.
Response to Communication pursuant to Article 94(3) issued against European application No. 09835355.0; dated Dec. 13, 2013.
Response to Communication pursuant to Article 94(3) issued against European application No. 09835355.0; dated Dec. 10, 2012.
A Textbook of Drug Design and Development; edited by Krogsgaard-Larsen and H. Bundgaard; Chapter 5; 'Design and Application of Prodrugs', by H. Bundgaard; 113-191; 1991.
Bundgaard, '(C) Means to Enhance Penetration (1) Prodrugs as a Means to Improve the Delivery of Peptide Drugs', Advanced Drug Delivery Reviews (1992); vol. 8; No. 1; 1-38.
Kakeya et al., Studies of Prodrugs of Cephalosporins. 1. Synthesis and Biological Properties of Glycyloxybenzoyloxymethyl and Glycylaminobenzoyloxymethyl Esters of 7β-[2-Aminothiazol-4-yl)-(Z)-2-methoxyiminoacetamido]-3-methyl-3-cephem-4-carboxylic Acid', Chem. Pharm Bull (1984); vol. 32 692-698.
Panunzio et al., 'Synthesis and Use of N-(Trimethylsily)imines', Organic Process Research & Development (1998); vol. 2; No. 1; 49-59.
Pasquinet et al., 'On the Metallation of 2-Isopropylpyridine', Tetrahedron (1998); vol. 54; No. 30; 8771-8782.
Green and Wuts; Protective Groups in Organic Synthesis, 3rd edition; John Wiley & Sons; 1999.
Methods in Enzymology; vol. 112; 309-396; edited by K. Widder et al., Academic Press; 1985.

* cited by examiner

ETHANAMINE COMPOUNDS AND METHODS OF USING THE SAME

CROSS-REFERENCE TO RELATED APPLICATIONS

This application is a Continuation Application of U.S. application Ser. No. 13/219,892, filed on Aug. 29, 2011, which is a Continuation Application of U.S. application Ser. No. 12/644,046, filed on Dec. 22, 2009, now U.S. Pat. No. 8,013,165 which claims the benefit under 35 U.S.C. §119(e) of Provisional Application 61/140,673 filed Dec. 24, 2008.

FIELD OF THE INVENTION

Disclosed herein is at least one ethanamine derivative, at least one pharmaceutical composition comprising at least one ethanamine derivative disclosed herein, and at least one method of using at least one ethanamine derivative disclosed herein for treating depression. The compounds may also have utility in the treatment of other diseases, including Parkinson's disease, pain states, such as neuropathic pain, as well as epilepsy and neurotrauma.

BACKGROUND OF THE INVENTION

Depression is a common mental disorder that occurs in persons of all genders, ages, and backgrounds, affecting about 121 million people worldwide. Symptoms of depression include, but are not limited to, depressed mood, loss of interest or pleasure, feelings of guilt or low self-worth, disturbed sleep or appetite, low energy, and poor concentration, or any combination thereof. These problems can become chronic or recurrent and lead to substantial impairments in an individual's ability to take care of his or her everyday responsibilities.

Depression is the leading cause of disability as measured by Years Lived with a Disability (YLDs) and the fourth leading contributor to the global burden of disease as measured by Disability Adjusted Life Years (DALYs; i.e., the sum of years of potential life lost due to premature mortality and the years of productive life lost due to disability) in 2000. By the year 2020, depression is projected to reach second place in the ranking of DALYs calculated for all ages, in both men and women. Today, depression is already the second cause of DALYs in the age category 15-44 years for both sexes combined. Whereas there are clearly a number of currently available treatments for depression, a significant proportion of patients are either incompletely treated (many residual symptoms remain) or do not respond to treatment at all. Thus, novel treatments for depression are needed. The present invention provides compounds, compositions, methods of preparing the same, and methods of treating depression. Such compounds would have additional utility in other disorders as well, including pain, Parkinson's disease, epilepsy and neurotrauma.

SUMMARY OF THE INVENTION

The present invention provides compounds
  2-methyl-1-phenyl-2-(pyridin-2-yl)propan-1-amine or a pharmaceutically acceptable salt thereof.
  (R)-2-methyl-1-phenyl-2-(pyridin-2-yl)propan-1-amine or a pharmaceutically acceptable salt thereof.
  (S)-2-methyl-1-phenyl-2-(pyridin-2-yl)propan-1-amine or a pharmaceutically acceptable salt thereof.

DESCRIPTION OF EMBODIMENTS

The features and advantages of the invention may be more readily understood by those of ordinary skill in the art upon reading the following detailed description. An advantage of the present invention is the prevention of stilbazole formation. Stilbazole is an undesirable by-product. The effects of stilbazole on humans is not yet fully appreciated but a product without stilbazole would be preferrable.

It is to be appreciated that certain features of the invention that are, for clarity reasons, described in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

Embodiments identified herein as exemplary are intended to be illustrative and not limiting.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth herein below. Unless otherwise indicated, the initial definition provided for a group or term applies each time such group or term is used individually. Throughout the specification, groups and substituents thereof may be chosen by one skilled in the field to provide stable moieties and compounds.

Unless specified otherwise herein, the nomenclature used herein generally follows the examples and rules stated in *Nomenclature of Organic Chemistry, Sections A, B, C, D, E, F, and H*, Pergamon Press, Oxford, 1979.

The term "about" means±5% of the value it modifies. For example, "about" 100 means 95 to 105.

The term "halogen" refers to chlorine, bromine, fluorine, and iodine.

The term "pharmaceutically acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The phrase "a compound of formula I, enantiomers thereof, pharmaceutically acceptable salts thereof, or mixtures thereof" or similar such phrases, refers to the free base of formula I or enantiomers thereof, pharmaceutically acceptable salts of formula I or enantiomers thereof, and/or mixtures of at least one free base of formula I or enantiomers thereof and at least one pharmaceutically acceptable salt of formula I or enantiomers thereof. Formula I is of the structure

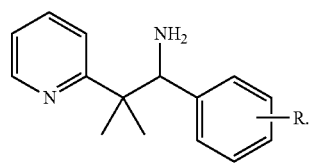

I

The term "therapeutically effective amount" refers to that amount of a compound sufficient to modulate one or more of the symptoms of the condition or disease being treated.

A selection of in vivo hydrolysable amide forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

The present invention provides the compound 2-methyl-1-phenyl-2-(pyridin-2-yl)propan-1-amine or a pharmaceutically acceptable salt thereof.

The present invention provides the compound (R)-2-methyl-1-phenyl-2-(pyridin-2-yl)propan-1-amine or a pharmaceutically acceptable salt thereof.

The present invention provides the compound (S)-2-methyl-1-phenyl-2-(pyridin-2-yl)propan-1-amine or a pharmaceutically acceptable salt thereof.

The present invention provides the compound 2-methyl-1-phenyl-2-(pyridin-2-yl)propan-1-amine fumarate.

The present invention provides the compound (R)-2-methyl-1-phenyl-2-(pyridin-2-yl)propan-1-amine fumarate.

The present invention provides the compound (S)-2-methyl-1-phenyl-2-(pyridin-2-yl)propan-1-amine fumarate.

The present invention provides a method of treating depression in a human which comprises administering to a person in need thereof a therapeutic effective amount of a compound or a pharmaceutically acceptable salt thereof, where the compound is 2-methyl-1-phenyl-2-(pyridin-2-yl)propan-1-amine.

The present invention provides a method of treating depression in a human which comprises administering to a person in need thereof a therapeutic effective amount of a compound or a pharmaceutically acceptable salt thereof, where the compound is (R)-2-methyl-1-phenyl-2-(pyridin-2-yl)propan-1-amine.

The present invention provides a method of treating depression in a human which comprises administering to a person in need thereof a therapeutic effective amount of a compound or a pharmaceutically acceptable salt thereof, where the compound is (S)-2-methyl-1-phenyl-2-(pyridin-2-yl)propan-1-amine.

The present invention provides a method of treating depression in a human which comprises administering to a person in need thereof a therapeutic effective amount of a compound or a pharmaceutically acceptable salt thereof, where the compound is 2-methyl-1-phenyl-2-(pyridin-2-yl)propan-1-amine fumarate.

The present invention provides a method of treating depression in a human which comprises administering to a person in need thereof a therapeutic effective amount of a compound or a pharmaceutically acceptable salt thereof, where the compound is (R)-2-methyl-1-phenyl-2-(pyridin-2-yl)propan-1-amine fumarate.

The present invention provides a method of treating depression in a human which comprises administering to a person in need thereof a therapeutic effective amount of a compound or a pharmaceutically acceptable salt thereof, where the compound is (S)-2-methyl-1-phenyl-2-(pyridin-2-yl)propan-1-amine fumarate.

The present invention provides a method of treating major depressive disorder in a human which comprises administering to a person in need thereof a therapeutic effective amount of a compound or a pharmaceutically acceptable salt thereof, where the compound is 2-methyl-1-phenyl-2-(pyridin-2-yl)propan-1-amine.

The present invention provides a method of treating major depressive disorder in a human which comprises administering to a person in need thereof a therapeutic effective amount of a compound or a pharmaceutically acceptable salt thereof, where the compound is (R)-2-methyl-1-phenyl-2-(pyridin-2-yl)propan-1-amine.

The present invention provides a method of treating major depressive disorder in a human which comprises administering to a person in need thereof a therapeutic effective amount of a compound or a pharmaceutically acceptable salt thereof, where the compound is (S)-2-methyl-1-phenyl-2-(pyridin-2-yl)propan-1-amine.

The present invention provides a method of treating major depressive disorder in a human which comprises administering to a person in need thereof a therapeutic effective amount of a compound or a pharmaceutically acceptable salt thereof, where the compound is 2-methyl-1-phenyl-2-(pyridin-2-yl)propan-1-amine fumarate.

The present invention provides a method of treating major depressive disorder in a human which comprises administering to a person in need thereof a therapeutic effective amount of a compound or a pharmaceutically acceptable salt thereof, where the compound is (R)-2-methyl-1-phenyl-2-(pyridin-2-yl)propan-1-amine fumarate.

The present invention provides a method of treating major depressive disorder in a human which comprises administering to a person in need thereof a therapeutic effective amount of a compound or a pharmaceutically acceptable salt thereof, where the compound is (S)-2-methyl-1-phenyl-2-(pyridin-2-yl)propan-1-amine fumarate.

The present invention provides a pharmaceutical composition comprising 2-methyl-1-phenyl-2-(pyridin-2-yl)propan-1-amine or a pharmaceutically acceptable salt thereof and a pharmaceutically acceptable adjuvant, carrier, or diluent.

The present invention provides a pharmaceutical composition comprising (R)-2-methyl-1-phenyl-2-(pyridin-2-yl)propan-1-amine or a pharmaceutically acceptable salt thereof and a pharmaceutically acceptable adjuvant, carrier, or diluent.

The present invention provides a pharmaceutical composition comprising (S)-2-methyl-1-phenyl-2-(pyridin-2-yl)propan-1-amine or a pharmaceutically acceptable salt thereof and a pharmaceutically acceptable adjuvant, carrier, or diluent.

The present invention provides a pharmaceutical composition comprising 2-methyl-1-phenyl-2-(pyridin-2-yl)propan-1-amine fumarate or a pharmaceutically acceptable salt thereof and a pharmaceutically acceptable adjuvant, carrier, or diluent.

The present invention provides a pharmaceutical composition comprising (R)-2-methyl-1-phenyl-2-(pyridin-2-yl)propan-1-amine fumarate or a pharmaceutically acceptable salt thereof and a pharmaceutically acceptable adjuvant, carrier, or diluent.

The present invention provides a pharmaceutical composition comprising (S)-2-methyl-1-phenyl-2-(pyridin-2-yl)propan-1-amine fumarate or a pharmaceutically acceptable salt thereof and a pharmaceutically acceptable adjuvant, carrier, or diluent.

The compounds of the present invention may be administered in the form of a prodrug which is broken down in the human or animal body to give a compound of the formula I. Examples of prodrugs include in vivo hydrolysable amides of a compound of formula I. Various forms of prodrugs are known in the art. For examples of such prodrug derivatives, see: a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs", by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77, 285 (1988); and e) N. Kakeya, et al., Chem Pharm Bull, 32, 692 (1984).

It will be understood that when compounds of the present invention contain a chiral center, the compounds of the invention may exist in, and be isolated as, enantiomeric or as a racemic mixture. The present invention includes any possible enantiomers, racemates or mixtures thereof, of the compounds of formula I. The optically active forms of the compound of the invention may be prepared, for example, by chiral chromatographic separation of a racemate, by synthesis from optically active starting materials or by asymmetric synthesis.

It will also be understood that certain compounds of the invention may exist in solvated, for example hydrated, as well as unsolvated forms. It will further be understood the present invention encompasses all such solvated forms of the compounds of formula I.

The present invention includes compounds in the form of salts, in particular acid addition salts. Suitable salts include all known pharmaceutically acceptable salts including those formed with both organic and inorganic acids. Thus, suitable salts include those formed from hydrochloric, hydrobromic, sulfuric, phosphoric, citric, tartaric, lactic, pyruvic, acetic, succinic, fumaric, maleic, methanesulphonic, and benzenesulphonic acids. Without being held to any specific salt form it appears that fumaric salts are particularly suitable.

The present invention also provides methods of treating depression including major depressive disorder in a human or other animal comprising administering a therapeutically effective amount of any of the compounds, isomers, enantiomers thereof, or pharmaceutically acceptable salts of the compounds or pharmaceutically acceptable salts of the isomers, enantiomers, described herein, or mixture of any of the compounds, isomers, enantiomers thereof, or pharmaceutically acceptable salts of the compounds or pharmaceutically acceptable salts of the isomers, enantiomers, described above. In some embodiments, the human or other animal will be in need thereof of such treatment.

In a further aspect, the invention provides methods of treating neurodegenerative disorders, for example Alzheimer's disease, Parkinson's disease, Huntington's disease, stroke, cerebral ischemia, cerebral palsy, the effects of hypoglycemia, epilepsy, dementia, AIDS related dementia, Olivoponto-cerebellar atrophy, perinatal asphyxia, anoxia, neuronal damage associated with substance abuse (for example narcotics or cocaine), retinopathies, schizophrenia, ischemic states after cardiac arrest or surgical operations, amyotrophic lateral sclerosis (ALS), coronary bypass disease, or fibromyalgia.

In a further aspect, the invention provides a low affinity NMDA antagonist, in particular a compound of formula I, in the manufacture of a medicament for use in the prevention or treatment of the above disorders, in particular for the prevention or treatment of depression including major depressive disorder.

The present invention also provides uses of any of the compounds, enantiomers thereof, or pharmaceutically acceptable salts of the compounds or enantiomers described above for treating depression in a human.

The present invention also provides compounds, enantiomers thereof, or pharmaceutically acceptable salts of the compounds or enantiomers described above for treating depression in a human.

The present invention also provides compounds, enantiomers thereof, or pharmaceutically acceptable salts of the compounds or enantiomers described above for use in the manufacture of a medicament for the treatment of depression.

The compounds according to the present invention may be administered by any route, including orally, intramuscularly, subcutaneously, topically, intranasally, intraperitoneally, intrathoracically, intravenously, epidurally, intrathecally, intracerebroventricularly and by injection into the joints. In one embodiment of the invention, the route of administration may be orally, intravenously or intramuscularly.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The term "composition" is intended to include the formulation of the active component with encapsulating material as a carrier providing a capsule in which the active component (with or without other carriers) is surrounded by a carrier which is thus in association with it. Similarly, cachets are included.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In some embodiments, the pharmaceutical composition is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The dosage will depend on the route of administration, the severity of the disease, age and weight of the patient and other factors normally considered by the attending physician, when determining the individual regimen and dosage level at the most appropriate for a particular patient.

Suitable daily dose ranges are from about 0.05 mg/kg to about 5.0 mg/kg. Unit doses may be administered conventionally once or more than once a day; for example, 2, 3, or 4 times a day; more usually 1 or 2 times a day. A typical dosing regimen would be oral, intramuscular or intravenous, once or twice a week to once or twice per day at 3.5 to 350 mg.

The pharmaceutical composition comprising the compound of the invention may conveniently be formulated as tablets, pills, capsules, syrups, powders or granules for oral administration; sterile parental or subcutaneous solutions, suspensions for parental administration; or suppositories for rectal administration; all of which are well known in the art.

For clinical use, the compounds of the invention are formulated into pharmaceutical formulations for oral, rectal, parenteral or any other mode of administration. The pharmaceutical formulation contains at least one compound of the invention in combination with one or more pharmaceutically acceptable ingredients. The carrier may be in the form of a solid, semi-solid or liquid diluent, or a capsule. These pharmaceutical preparations are a further object of the invention. Depending on the mode of administration, the pharmaceutical composition can comprise from about 0.05% w to about 99% w (percent by weight), or from about 0.05% w to about 80% w, or from about 0.10% w to about 70% w, or from about 0.10% w to about 50% w, of active ingredient, all percentages by weight being based on total composition.

In the preparation of pharmaceutical formulations containing at least one compound of the present invention in the form of dosage units for oral administration the compound selected may be mixed with solid, powdered ingredients, or another suitable ingredient, as well as with disintegrating agents and lubricating agents. The mixture is then processed into granules or pressed into tablets.

Soft gelatin capsules may be prepared with capsules containing a mixture of the active compound or compounds of the invention. Hard gelatin capsules may contain granules of the active compound. Hard gelatin capsules may also contain the active compound in combination with solid powdered ingredients.

Dosage units for rectal administration may be prepared (i) in the form of suppositories which contain the active substance mixed with a neutral fat base; (ii) in the form of a gelatin rectal capsule which contains the active substance in a mixture with suitable vehicles for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g., solutions or suspensions containing the active ingredient. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of at least one compound of the invention in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

Combinations wherein a compound of formula (I) or a pharmaceutically acceptable salt, solvate or in vivo hydrolysable amide thereof, or a pharmaceutical composition or formulation comprising a compound of formula (I) is administered concurrently, simultaneously, sequentially or separately with another pharmaceutically active compound or compounds selected from the following:

(i) antidepressants such as agomelatine, amitriptyline, amoxapine, bupropion, citalopram, clomipramine, desipramine, doxepin, duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(ii) atypical antipsychotics including for example quetiapine, lithium and equivalents thereof and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(v) anticonvulsants including for example carbamazepine, valproate, lamotrogine, gabapentin and equivalents and pharmaceutically active isomer(s) and metabolite(s) thereof.

(vi) Alzheimer's therapies including for example donepezil, memantine, tacrine and equivalents and pharmaceutically active isomer(s) and metabolite(s) thereof.

(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.

(viii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof.

(ix) stroke therapies including for example abciximab, activase, NXY-059, citicoline, crobenetine, desmoteplase, repinotan, traxoprodil and equivalents and pharmaceutically active isomer(s) and metabolite(s) thereof.

(x) over active bladder urinary incontinence therapies including for example darafenacin, falvoxate, oxybutynin, propiverine, robalzotan, solifenacin, tolterodine and equivalents and pharmaceutically active isomer(s) and metabolite(s) thereof.

(xi) neuropathic pain therapies including for example gabapentin, lidoderm, pregablin and equivalents and pharmaceutically active isomer(s) and metabolite(s) thereof.

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.

(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

(xv) analgesics including for example acetaminophen, ibuprofen, naproxen, hydrocodone, oxycodone, diclofenac, piroxicam, etodolac, fenoprofen, ketoprofen, ketorolac, loxoprofen, meclofenamate, meloxicam, gabapentin, paracetamol, morphine, fentyl, cyclooxygenase-2-inhibitors, celecoxib, etoricoxib, lumiracoxib, rofecoxib, valdecoxib, codeine, propoxyphene, tramadol and equivalents and pharmaceutically active isomer(s) and metabolite(s) thereof.

Such combination products employ the compounds of this invention within the dosage range described herein and the other pharmaceutically active compound or compounds within approved dosage In general, compounds of the present invention can be prepared in accordance with the following Schemes and the general knowledge of one skilled in the art and/or in accordance with the methods set forth in the Examples that follow. Solvents, temperatures, pressures, and other reaction conditions may readily be selected by one of ordinary skill in the art. Starting materials are commercially available or readily prepared by one skilled in the art.

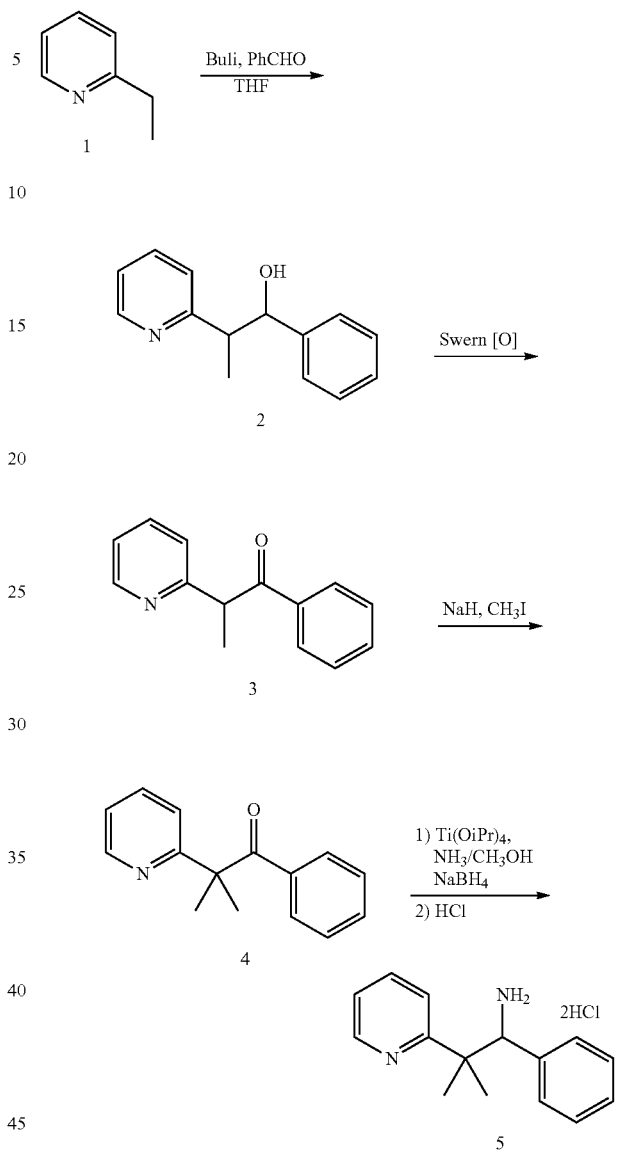

Step 1: A compound in accordance with formula II can be obtained by treating 2-ethylpyridine with a suitable strong base, such as, butyl lithium, in an appropriate solvent, such as THF followed by an aromatic aldehyde.

Step 2: A compound in accordance with formula III can be obtained by treating a compound in accordance with formula II with an appropriate oxidizing agent, such as a Swern oxidation agent, in an appropriate solvent, such as DCM.

Step 3: A compound in accordance with formula IV can be obtained by treating a compound in accordance with formula III with an appropriate strong base, such as sodium hydride, in an appropriate solvent, such as THF, and an appropriate alkylating agent, such as methyl iodide.

Step 4: A compound in accordance with formula I can be obtained by treating a compound in accordance with formula IV with an appropriate amine source, such as ammonia, in an appropriate solvent, such as methanol, and an appropriate reducing agent, such as sodium borohydride.

Scheme II

[Structure V: R-phenyl-CH=N-Si(R$_5$)$_3$]

V

[Structure VI: 2-pyridyl-C(CH$_3$)$_2$-K]

VI

[Structure I: 2-pyridyl-C(CH$_3$)$_2$-CH(NH$_2$)-phenyl-R]

I

A compound in accordance with formula I can be obtained by treating a compound in accordance with formula V as prepared according to Panunzio, M. and Zarantonelo, P. Org. Proc. Res. Dev. (1998) 2 49-59) with a compound in accordance with formula VI prepared according to Pasquinet et al, Tetrahedron 54 (1998) 8771-8782) in an appropriate solvent, such as THF.

The present invention also provides methods of preparing compounds described above comprising:

a) treating 2-ethylpyridine with a suitable strong base in an appropriate solvent, followed by an aromatic aldehyde to produce a compound of formula II

[Structure II: 2-pyridyl-CH(CH$_3$)-CH(OH)-phenyl-R]

II wherein R corresponds to the optional substituent on Ar$_2$ in the compound of claim 1;

b) treating the compound of formula II with an appropriate oxidizing agent in an appropriate solvent to produce a compound of formula III

[Structure III: 2-pyridyl-CH(CH$_3$)-C(O)-phenyl-R]

III c) treating the compound of formula III with an appropriate strong base in an appropriate solvent and an appropriate alkylating agent to produce a compound of formula IV.

[Structure IV: 2-pyridyl-C(CH$_3$)$_2$-C(O)-phenyl-R]

IV and d) treating the compound of formula IV with an appropriate amine source in an appropriate solvent and an appropriate reducing agent to produce the compound described above.

In some embodiments, in a) the suitable strong base is butyl lithium and the solvent is tetrahydrofuran (THF).

In some embodiments, in b) the oxidizing agent is a Swern oxidation agent and the solvent is DCM.

In some embodiments, in c) the strong base is sodium hydride, the solvent is tetrahydrofuran (THF), and the alkylating agent is methyl iodide.

In some embodiments, in d) the amine source is ammonia, the solvent is methanol, and the reducing agent is sodium borohydride.

The present invention also provides methods of preparing compounds described above comprising treating a compound of formula V

[Structure V: R-phenyl-CH=N-Si(R$_5$)$_3$]

V wherein R corresponds to the optional substituent on Ar$_2$ in the compounds described above, and wherein R$_5$ is methyl, with a compound of formula VI

[Structure VI: 2-pyridyl-C(CH$_3$)$_2$-K]

VI wherein K is potassium, or the potassium counterion, in an appropriate solvent to produce the compounds described above.

In some embodiments, the solvent is tetrahydrofuran (THF).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration, see Green and Wuts, Protective Groups in Organic Synthesis, 3rd ed., John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group, which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

The protecting groups may be removed at any convenient stage in the synthesis using conventional techniques well known in the chemical art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.). Unless otherwise stated, operations are carried out at room or ambient temperature (18-25° C.).

Unless otherwise noted, commercial reagents used in preparing the example compounds are used as received without additional purification.

Unless otherwise noted, the solvents used in preparing the example compounds are commercial anhydrous grades and are used without further drying or purification.

Unless otherwise noted, the following method is used to determine nuclear magnetic resonance spectrometry: a Varian Unity Inova 400 spectrometer operating at 400 MHz for $^1$H equipped with a 5 mm inverse detection triple resonance probe for detection of $^1$H, $^{13}$C, $^{31}$P with the magnetic field provided by a 9.4 Tesla Oxford instruments super-conducting magnet and a Sun Microsystems SunBlade 1000 workstation as host. Chemical shifts are reported in parts-per-million ($\delta$) from a tetramethylsilane internal standard.

Unless otherwise indicated, the following method is used for mass spectrometer detection: a Waters ZMD quadrupole mass spectrometer linked to a Waters 1525 LC system with Waters 996 diode array detector. Sample injection is done by a Waters 2700 autosampler. The spectrometer has an electrospray source operating in positive and negative ion mode. Additional detection is achieved using a Sedex 65 ELS detector. All m/z ratios are reported as the M+1 ion.

Chiral chromatography to separate enantiomers is performed using a Berger multi gram II supercritical fluid chromatography (SFC) system equipped with an ADH column, 21.2×250 mm in size, running an isocratic gradient of 15% isopropanol with 0.5% isopropylamine in $CO_2$, a flow rate of 70 mL/minute and UV detection at 230 nm.

The names of the compounds exemplified herein are generated using AutoNom 2000 within ISIS/Draw. AutoNom (Automatic Nomenclature) is a chemical-name-generating program that assigns systematic IUPAC (International Union of Pure and Applied Chemistry) chemical names to drawn structures at the press of a button.

The following abbreviations are employed herein: ACN: Acetonitrile; AcOH: acetic acid; $CDCl_3$; deuterated chloroform; $D_3OD$: deuterated methanol; DCM: dichloromethane; DMF: N,N-dimethylformamide; DMSO: dimethyl sulfoxide; DMSO-d6: deuterated dimethyl sulfoxide; ELS: evaporative light scattering; EtOAc: ethyl acetate; equiv: equivalent; Ex.: Example; HPLC: high performance liquid chromatography; HCl: hydrochloric acid; $H_2O$: water; $H_2SO_4$: sulfuric acid; LAH: Lithium aluminum hydride; LCMS: liquid chromatography mass spectral detection; m/z: mass to charge ratio; LDA: lithium diisopropyl amide; MeOH: methanol; $MgSO_4$: magnesium sulfate; min.: minutes; MS: mass spectrum; M.p.: melting point; $NaBH_4$:

sodium borohydride; n-BuLi: Lithium-1-butanide; NaHCO₃: sodium bicarbonate; NaOH: sodium hydroxide; Na₂SO₄: sodium sulfate; NH₄Cl: ammonium chloride; NMR: nuclear magnetic resonance; N2: nitrogen gas: room temperature; rt=retention time; sat.: saturated; THF: tetrahydrofuran; and UV: Ultraviolet.

Example 1A

2-methyl-1-phenyl-2-(pyridin-2-yl)propan-1-amine via Scheme I

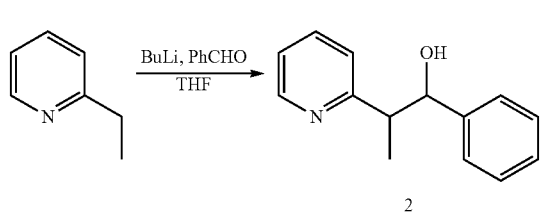

1-Phenyl-2-(pyridin-2-yl)propan-1-ol (2): n-Butyllithium (2.5 M, 15.0 mL, 36.0 mmol) is added drop wise to a solution of 2-ethylpyridine (4.1 mL, 36.0 mmol) in THF (56 mL) at −40° C. The resulting dark red solution is kept at −30° C. to −20° C. for 1 hour and then cooled to −60° C. A solution of benzaldehyde (3.7 mL, 36.0 mmol) in THF (10 mL) is added drop wise. The reaction mixture is allowed to warm up to 0° C. for 1 hour and then quenched with aqueous NH₄Cl solution. The mixture is separated and the aqueous phase is extracted with ethyl acetate (2×50 mL). The extracts are combined, dried, concentrated and purified by column chromatography (hexane/ethyl acetate 10:1 to 1:1) to give 2 (7.0 g, 91%) as a yellow oil. This mixture contained two diastereoisomers (3:1). ¹H NMR (300 MHz, CDCl₃) for the major isomer: δ 1.14 (d, J=7.2 Hz, 3H), 2.98 (q, J=6.9 Hz, 1H), 4.70-4.75 (m, 1H), 5.13-5.16 (m, 1H), 6.80-7.39 (m, 8H), 8.34 (d, J=4.8 Hz, 1H).

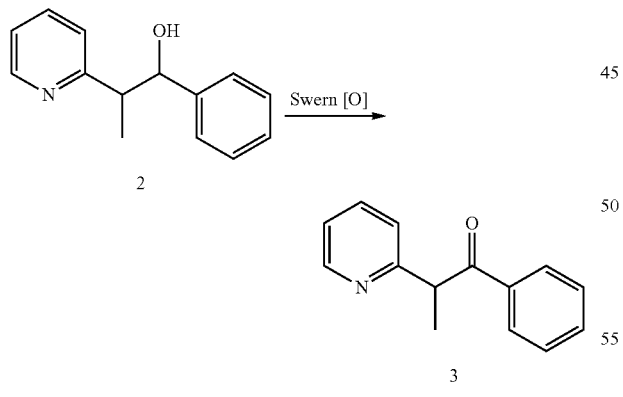

1-Phenyl-2-(pyridin-2-yl)propan-1-one (3): A solution of DMSO (5.5 mL, 77.5 mmol) in dichloromethane (10 mL) is added drop wise to a solution of oxalyl chloride (3.3 mL, 39.0 mmol) in dichloromethane (100 mL) with the internal temperature under −60° C. The reaction mixture is stirred for 15 minutes and then a solution of 1-phenyl-2-(pyridin-2-yl)propan-1-ol (2) (7.0 g, 32.8 mmol) in dichloromethane (10 mL) is added slowly to keep the internal temperature under −60° C. After 30 minutes, triethylamine (22.3 mL, 0.16 mol) is added slowly at −78° C. After 15 minutes, the reaction is allowed to warm up to 0° C. for 30 minutes and then quenched with water. The mixture is separated and the aqueous phase is extracted with dichloromethane (2×50 mL). The extracts are combined, washed with brine, dried, concentrated and purified by column chromatography (hexane/ethyl acetate 10:1 to 4:1) to give 3 (6.4 g, 91%) as a yellow oil. ¹H NMR (300 MHz, CDCl₃): δ 1.51-1.54 (m, 3H), 4.84-4.92 (m, 1H), 7.03-708 (m, 1H), 7.18-7.20 (m, 2H), 7.30-7.35 (m, 1H), 7.40-7.43 (m, 1H), 7.52-7.57 (m, 1H), 7.95-7.98 (m, 2H), 8.47-8.48 (m, 1H).

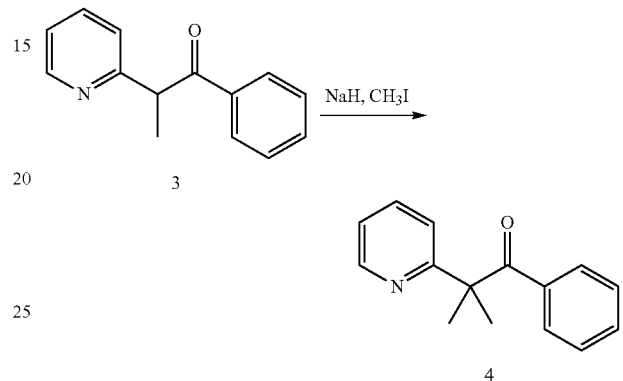

2-Methyl-1-phenyl-2-(pyridin-2-yl)propan-1-one (4): A solution of compound 3 (3.0 g, 14.2 mmol) in THF (10 mL) is added to a suspension of sodium hydride (60%, 0.63 g, 15.6 mmol) in THF (60 mL) at 0° C. The reaction mixture is kept at the same temperature for 2 hours and methyl iodide (0.93 mL, 14.9 mmol) is added at 0° C. The reaction mixture is allowed to warm up to room temperature overnight and then quenched with water. The mixture is separated and the aqueous phase is extracted with ethyl acetate (2×40 mL). The extracts are combined, washed with brine, dried, concentrated and purified by column chromatography (hexane/ethyl acetate 50:1 to 4:1) to give 4 (2.2 g, 69%) as a yellow solid.

2-Methyl-1-phenyl-2-(pyridin-2-yl)propan-1-amine dihydrochloride (1): Freshly distilled Ti(O-iPr)₄ (11.2 mL, 38.0 mmol) is added to a solution of 4 (4.4 g, 19.0 mmol) in ammonia in methanol (7 M, 30 mL). The reaction mixture is stirred at room temperature for 12 hours and then cooled to 0° C. NaBH₄ (1.4 g, 38.0 mmol) is added slowly. The reaction is then warmed up to room temperature for 3 hours and then poured into ammonium hydroxide (50 mL). The mixture is extracted with ethyl acetate (2×50 mL). The extracts are combined, washed with brine, dried, concentrated and purified by column chromatography (pretreated with triethylamine) (DCM/methanol 20:1) to yield the free base of 1 (3.0 g) as a yellow oil. This oil is dissolved in isopropyl acetate (50 mL) and a solution of 5-6 N HCl in isopropyl alcohol (4.0 mL) is added. The mixture is concentrated, dissolved in methanol, concentrated and triturated in ether to yield 1 (4.0 g, 60%) as a white solid. M.p.=188° C. $^1$H NMR (300 MHz, CD$_3$OD): δ 1.59 (s, 3H), 1.76 (s, 3H), 5.09 (s, 1H), 7.25-7.28 (m, 2H), 7.38-7.40 (m, 3H), 8.00 (t, J=6.6 Hz, 1H), 8.11 (d, J=6.9 Hz, 1H), 8.56 (t, J=7.8 Hz, 1H), 8.77 (d, J=5.7 Hz, 1H); $^{13}$C NMR (75 MHz, CD$_3$OD): δ 22.2, 22.6, 43.7, 62.4, 126.2, 126.4, 128.1, 128.9, 129.6, 133.3, 142.9, 146.9. MS: m/z 227.

Example 1B 2-methyl-1-phenyl-2-(pyridin-2-yl)propan-1-amine via Scheme II

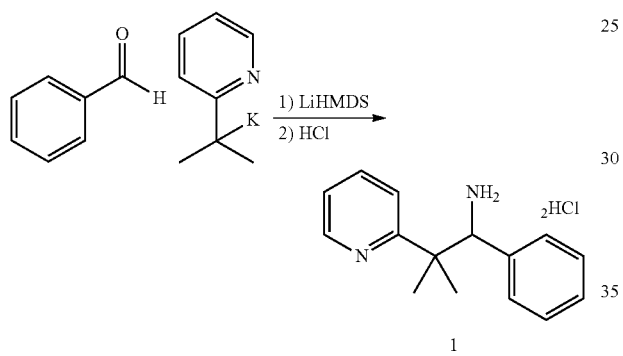

2-Methyl-1-phenyl-2-(pyridin-2-yl)propan-1-amine dihydrochloride. To a stirred solution of benzaldehyde (3.44 mL, 33.92 mmol) in THF (35 mL) is added a THF solution of lithium bis(trimethylsilyl)amide (37.3 mL, 37.32 mmol) at 0° C. The mixture is stirred at 0° C. for 2 hours. To the resulting solution is added (2-(pyridin-2-yl)propan-2-yl)potassium (6.48 g, 40.71 mmol) at −20 to −15° C. drop wise prepared in the following manner: in a dried, nitrogen-flushed flask was placed potassium 2-methylpropan-2-olate (61.9 mL, 61.89 mmol) (1.0 M in THF) and diisopropylamine (8.75 mL, 61.89 mmol). The mixture is cooled to −20° C. and BuLi (30.9 mL, 49.51 mmol) is slowly added to give a yellow solution. The reaction mixture is then cooled to −50° C. and 2-isopropylpyridine (5 g, 41.26 mmol) is added and the mixture stirred 30 minutes. The mixture is then stirred at −20° C. for 30 minutes, and sat. NH$_4$Cl is added. The mixture is extracted with EA (3×). Combined EA are washed with sat. NaCl, dried over Na$_2$SO$_4$, filtered and concentrated by ISCO column (240 g), eluting with 0-70% EA/Hex, then 5% MeOH/DCM to give 2-methyl-1-phenyl-2-(pyridin-2-yl)propan-1-amine (6.07 g, 79%) as an yellow oil. This oil is dissolved in isopropyl acetate (50 mL) and a solution of 5-6 N HCl in isopropyl alcohol (4.0 mL) is added. The mixture is concentrated, dissolved in methanol, concentrated and triturated in ether to yield 1 (4.0 g, 60%) as a white solid. M.p.=188° C. $^1$H NMR (300 MHz, CD$_3$OD): δ 1.59 (s, 3H), 1.76 (s, 3H), 5.09 (s, 1H), 7.25-7.28 (m, 2H), 7.38-7.40 (m, 3H), 8.00 (t, J=6.6 Hz, 1H), 8.11 (d, J=6.9 Hz, 1H), 8.56 (t, J=7.8 Hz, 1H), 8.77 (d, J=5.7 Hz, 1H); $^{13}$C NMR (75 MHz, CD$_3$OD): δ 22.2, 22.6, 43.7, 62.4, 126.2, 126.4, 128.1, 128.9, 129.6, 133.3, 142.9, 146.9. MS: m/z 227.

Example 2

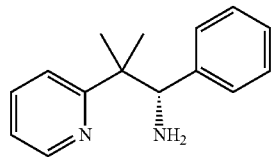 [SMILES: CC(C)(c1ccccn1)[C@@H](N)c1ccccc1]

(S)-2-methyl-1-phenyl-2-(pyridin-2-yl)propan-1-amine is prepared starting from racemic 2-methyl-1-phenyl-2-(pyridin-2-yl)propan-1-amine using chiral SFC chromatography. This oil is dissolved in isopropyl acetate and a solution of 5-6 N HCl in isopropyl alcohol is added. The mixture is concentrated, and triturated in ether to yield the title compound as a white solid. M.p.=188° C. $^1$HNMR (300 MHz, CD$_3$OD): δ 1.59 (s, 3H), 1.76 (s, 3H), 5.09 (s, 1H), 7.25-7.28 (m, 2H), 7.38-7.40 (m, 3H), 8.00 (t, J=6.6 Hz, 1H), 8.11 (d, J=6.9 Hz, 1H), 8.56 (t, J=7.8 Hz, 1H), 8.77 (d, J=5.7 Hz, 1H). MS: m/z 227.

An alternative route to generate Example 2 is described below

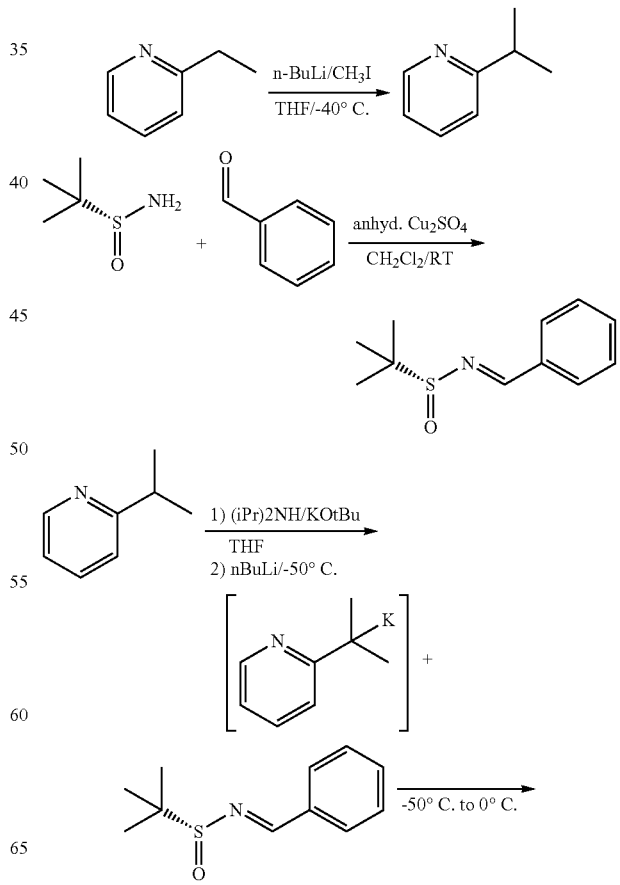

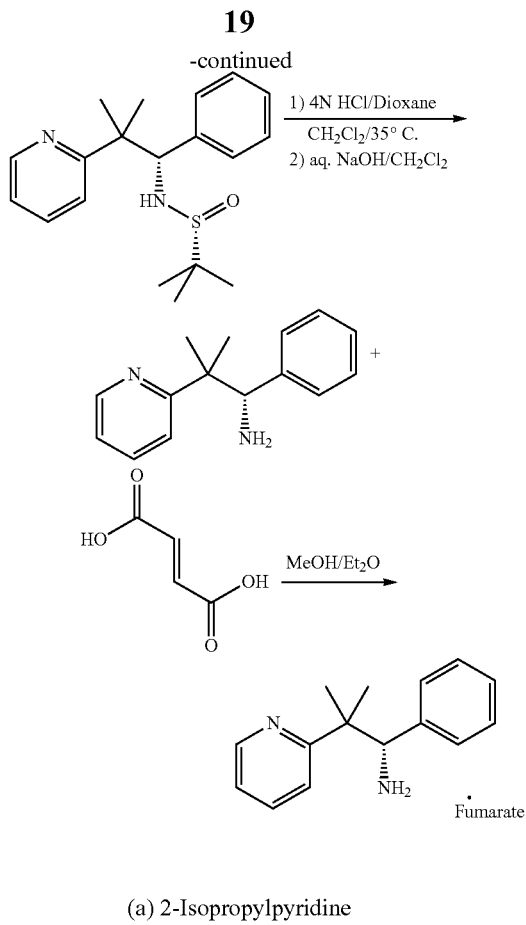

(a) 2-Isopropylpyridine

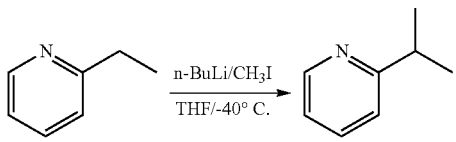

2-Isopropylpyridine was prepared by the method of P. Rocca, et. al. (Tetrahedron Vol. 54, pp. 8771-8782 (1998). A solution of 2-ethylpyridine (1000 g, 9.332 moles) in anhydrous Tetrahydrofuran (6000 mL) was cooled to −35° C. by a dry ice/acetone bath. n-Butyllithium (3970 mL of 2.5 Molar, 9.925 moles) was added at a fast drop wise rate over a period of 1.5 hours, while maintaining the internal temperature at −20° C. to −25° C. Stirring was continued for an additional 1.5 hours at −20° C., then the reaction was cooled to −45° C. Iodomethane (642 mL, 1458 g, 10.272 moles) was added at a moderate drop wise rate over a period of 1.5 hours, while maintaining the reaction temperature between −40° C. and −45° C. After the addition was complete, the mixture was allowed to stir for an additional 2 hours at −40° C., then was quenched by the fast drop wise addition of water (4000 mL) added over a period of 30 minutes. The reaction mixture was cooled to 0° C. and treated with concentrated Hydrochloric acid (1150 mL) added over a period of 15 minutes. The mixture was allowed to stir for an additional hour while warming to 15° C., then was transferred to a separatory funnel with diethyl ether (2000 mL), and the layers separated. The aqueous phase was further washed with diethyl ether (3×1000 mL), then made basic (pH=9) by treatment with solid potassium carbonate. The aqueous mixture was extracted with diethyl ether (4×1000 mL). The combined extracts were washed with saturated brine (1000 mL) then dried (anhydrous magnesium sulfate). Filtration, followed by removal of the solvent under reduced pressure at room temperature, gave the crude product as a reddish-orange liquid (~2000 mL). This crude product was distilled (twice) at atmospheric pressure through a three inch, glass vigreaux column, collecting the desired 2-isopropylpyridine (b.p. 158-163° C.) as a light yellow liquid (926 g, 82% yield). $^1$H NMR (300 MHz, CHLOROFORM-d) δ ppm 8.53 (d, J=4.22 Hz, 1H) 7.59 (td, J=7.59, 1.69 Hz, 1H) 7.16 (d, J=8.01 Hz, 1H) 7.08 (ddd, J=7.38, 4.85, 0.84 Hz, 1H) 2.94-3.25 (m, J=6.91, 6.91, 6.91, 6.91, 6.91, 6.74 Hz, 1H) 1.31 (d, J=6.74 Hz, 6H).

(b)
(R,E)-N-benzylidene-2-methylpropane-2-sulfinamide

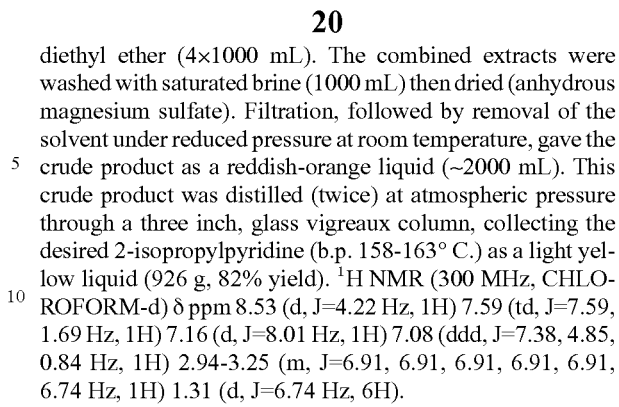

To a solution of (R)-2-methylpropane-2-sulfinamide (1032 g, 8.515 moles) in dichloromethane (14000 mL) was added benzaldehyde (1000 g, 9.423 moles) in one portion at room temperature. Anhydrous copper (II) sulfate (2718 g, 17.029 moles) was added in portions as a solid over a 10-minute period, and washed down with additional dichloromethane (1000 mL). The reaction mixture was allowed to stir for 45 hours at room temperature, and was checked for completion by HPLC. The mixture was filtered through a pad of Celite to remove the copper (II) sulfate. The filter cake was washed with dichloromethane (4×1500 mL), and the combined filtrates concentrated under reduced pressure to a cloudy yellow oil (1914 g, 107% of theory). The crude product was subjected to chromatography over silica gel, eluting with a gradient of 0-10% ethyl acetate in dichloromethane to yield the purified sulfinamide as a pale yellow oil (1563 g, 88% yield). 1H NMR (300 MHz, CHLOROFORM-d) δ ☐ppm 8.60 (s, 1H) 7.85 (dd, J=7.80, 1.48 Hz, 2H) 7.40-7.62 (m, 3H) 1.27 (s, 9H). MS: m/z 210.

(c) (R)-2-methyl-N—((S)-2-methyl-1-phenyl-2-(pyridine-2-yl)propyl)propane-2-sulfinamide

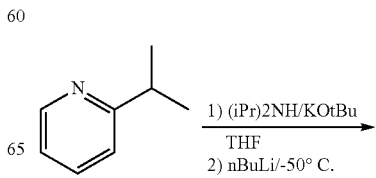

-continued

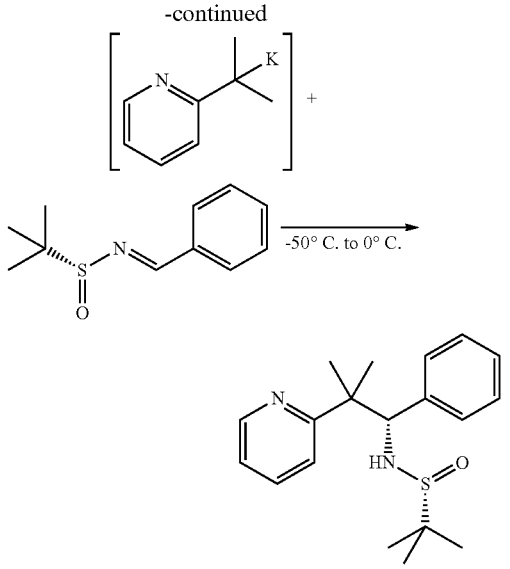

To a 1.0 Molar solution of potassium t-butoxide in tetrahydrofuran (3000 mL, 3.000 moles) was added diisopropylamine (425 mL, 306.8 g, 3.032 moles). The resulting solution was cooled by a dry ice/acetone bath to −50° C. n-Butyllithium solution (980 mL of 2.5 Molar, 2.450 moles) was added drop wise over a period of 40 minutes, giving a bright orange solution. The mixture was allowed to stir for an additional 20 minutes at −25° C., then was cooled back down to −55° C. 2-isopropylpyridine (240.0 g, 1.981 moles) was then added drop wise over a period of 20 minutes while maintaining the internal temperature between −50° C. to −55° C., giving a deep, reddish-purple solution. The mixture was allowed to stir for an additional 2 hours at −50° C., then was used directly in the next step.

To the cooled (−50° C.) mixture containing the 2-Isopropylpyridyl anion was added a solution of (R,E)-N-benzylidene-2-methylpropane-2-sulfinamide (360.0 g, 1.720 moles) in anhydrous tetrahydrofuran (3000 mL), drop wise over a period of 3 hours while maintaining the internal temperature between −50° C. and −55° C. The reaction mixture was allowed to warm gradually over 3 hours to 0° C., then checked for completion by working up an aliquot and checking by HPLC. The reaction was quenched by treatment with saturated sodium bicarbonate solution (3000 mL), added drop wise over 20 minutes. After stirring for an additional 30 minutes, the mixture was further diluted with water (3000 mL), and divided into three portions (~4500 mL each). Each portion was partitioned with ethyl acetate (1000 mL), and the layers separated. The combined aqueous layer was further extracted with ethyl acetate (3×1000 mL). The combined organic extracts were washed with saturated brine (1500 mL), then dried (anhydrous magnesium sulfate). Filtration, followed by removal of the solvent under reduced pressure, left the crude product as a cream-colored solid (575.8 g, 101.3% crude yield), which was a 9:1 mixture of diastereomers. The crude material was recrystallized from a mixture of Hexane/EtOAc (2:1) to give pure desired single diastereomer (371.9 g, 65.4% yield). 1H NMR (300 MHz, CHLOROFORM-d) δ ppm 8.62 (dd, J=4.85, 1.05 Hz, 1H) 7.52 (td, J=7.80, 2.11 Hz, 1H) 7.09-7.19 (m, 4H) 6.99 (d, J=8.01 Hz, 1H) 6.85-6.94 (m, 2H) 5.80 (d, J=8.01 Hz, 1H) 4.49 (d, J=8.43 Hz, 1H) 1.46 (s, 3H) 1.33 (s, 3H) 1.10 (s, 9H). MS: m/z 331.

(d) (S)-2-methyl-1-phenyl-2-(pyridine-2-yl)propan-1-amine

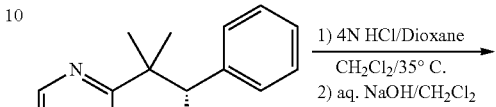

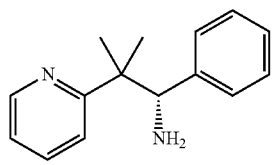

To a solution of (R)-2-methyl-N—((S)-2-methyl-1-phenyl-2-(pyridin-2-yl)propyl)propane-2-sulfinamide (1200 g, 3.631 moles) dissolved in dichloromethane (12000 mL) was added 4N hydrogen chloride/dioxane solution (3000 mL, 12.00 moles) in a steady stream over a period of 1 hour at room temperature. A thick suspension formed, which was continued stirring for 1.5 hours at 32° C.; at which point Methanol (1000 mL) was added to improve stirring. After 30 minutes additional stirring, all of the solids dissolved, giving a clear amber solution and indicating complete reaction. The solvents were removed under reduced pressure leaving a gummy amber residue. The residue was taken up in distilled water (5000 mL), and the resulting solution washed with diethyl ether (2×1000 mL) to remove neutral impurities. The acidic solution was treated with solid Sodium hydroxide (400 g, 10.00 moles) until strongly basic (pH=11). The resulting aqueous mixture was extracted with dichloromethane (2×1000 mL, then 2×500 mL). The combined organic extracts were dried (anhydrous magnesium sulfate). Filtration, followed by removal of the solvent under reduced pressure, left a thick amber syrup. This residue was further dried under high vacuum to yield the crude de-protected amine (880.9 g, 107.2% of theory). 1H NMR (300 MHz, CHLOROFORM-d) δ ppm 8.64 (d, J=3.79 Hz, 1H) 7.57 (td, J=7.69, 1.90 Hz, 1H) 7.05-7.30 (m, 7H) 4.48 (s, 1H) 1.47 (br.s., 2H) 1.36 (s, 3H) 1.25 (s, 3H). MS: m/z 227.

(e) (S)-2-methyl-1-phenyl-2-(pyridine-2-yl)propan-1-amine Fumarate Salt

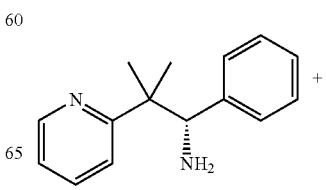

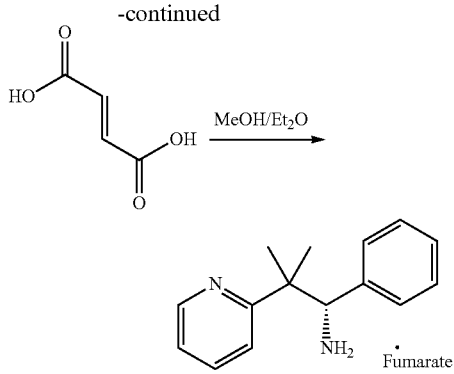

(S)-2-methyl-1-phenyl-2-(pyridine-2-yl)propan-1-amine (821.7 g, 3.63 moles) was dissolved in methanol (5000 mL) giving a reddish-orange solution. The solution was treated with Norit decolorizing Carbon (50 g) and stirred at gentle reflux for 2 hours. The hot solution was filtered through a pad of Celite, giving a light yellow filtrate. The Carbon filter cake was further washed with hot methanol (2×1000 mL), and the washes combined with the original filtrate. The decolorized solution was treated with fumaric acid (421.4 g, 3.63 moles), added as a dry solid over a period of 5 minutes. The solution was allowed to stir at room temperature for 30 minutes, then was concentrated under reduced pressure to remove most of the methanol (6000 mL removed). The resulting thick amber syrup was diluted gradually with vigorous stirring with diethyl ether (7000 mL) until crystallization ensued. The mixture was stirred vigorously until a very healthy crop of crystals had formed. The mixture was then further diluted with additional diethyl ether (2000 mL, total volume of 9000 mL) with vigorous stirring to complete the crystallization. The crystals were collected by suction filtration and pulled free of liquors. The crystals were re-suspended in a mixture of 9:1 diethyl ether/methanol (2000 mL) and stirred vigorously for several minutes, then re-filtered and pulled dry. The process was repeated a second time. The white crystals obtained from this treatment were dried to constant weight in the vacuum oven at 60° C. to yield (S)-2-methyl-1-phenyl-2-(pyridine-2-yl)propan-1-amine fumarate salt (1179.3 g, 95% yield). 1H NMR (300 MHz, DMSO-d 6) δ ppm 9.19 (br. s., 3H) 8.62 (d, J=3.37 Hz, 1H) 7.71 (td, J=7.80, 1.69 Hz, 1H) 7.17-7.39 (m, 5H) 6.94-7.17 (m, 2H) 6.51 (s, 2H) 4.64 (s, 1H) 1.35 (s, 3H) 1.26 (s, 3H). $^{13}$C NMR (75 MHz, DMSO-d 6): δ ppm 23.7, 25.7, 43.8, 62.7, 121.3, 122.3, 128.0, 128.1, 128.6, 135.5, 137.4, 137.8, 148.7, 164.9, 168.3. MS: m/z 227.

Example 3

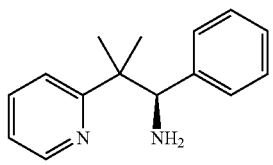 [SMILES: CC(C)(c1ccccn1)[C@H](N)c1ccccc1]

(R)-2-methyl-1-phenyl-2-(pyridin-2-yl)propan-1-amine is prepared starting from racemic 2-methyl-1-phenyl-2-(pyridin-2-yl)propan-1-amine using chiral SFC chromatography. This oil is dissolved in isopropyl acetate and a solution of 5-6 N HCl in isopropyl alcohol is added. The mixture is concentrated, and triturated in ether to yield the title compound as a white solid. M.p.=188° C. $^{1}$HNMR (300 MHz, CD$_3$OD): δ 1.59 (s, 3H), 1.76 (s, 3H), 5.09 (s, 1H), 7.25-7.28 (m, 2H), 7.38-7.40 (m, 3H), 8.00 (t, J=6.6 Hz, 1H), 8.11 (d, J=6.9 Hz, 1H), 8.56 (t, J=7.8 Hz, 1H), 8.77 (d, J=5.7 Hz, 1H). MS: m/z 227.

Biological Evaluation

NMDA receptor antagonist activity can be measured in vitro by assaying a compound's ability to inhibit binding of the receptor antagonist 10,11-dihdro-5-methyl-5H-dibenzo [a,d]-cyclohepten-5,10-imine (MK801) to the receptor. The method is described by Foster and Wong, Br. J. Pharmacol. 91, 403-409 (1987).

The IC$_{50}$ values of examples 1-6 are set forth in Table 1.

TABLE 1

| Compound of Example # | MK801 Binding IC$_{50}$ (uM) |
|---|---|
| Example 1 | 12 |
| Example 2 | 6.4 |
| Example 3 | 35 |

What is claimed is:

1. 2-Methyl-1-phenyl-2-(pyridin-2-yl)propan-1-amine or a pharmaceutically acceptable salt thereof.

2. A compound as claimed in claim 1 which is 2-methyl-1-phenyl-2-(pyridin-2-yl)propan-1-amine or a hydrochloric, hydrobromic, sulfuric, phosphoric, citric, tartaric, lactic, pyruvic, acetic, succinic, fumaric, maleic, methanesulphonic or benzenesulphonic acid salt thereof.

3. A compound as claimed in claim 1 which is 2-methyl-1-phenyl-2-(pyridin-2-yl)propan-1-amine fumarate.

4. A compound as claimed in claim 1 which is 2-methyl-1-phenyl-2-(pyridin-2-yl)propan-1-amine.

5. A compound as claimed in claim 1 which is (S)-2-methyl-1-phenyl-2-(pyridin-2-yl)propan-1-amine or a pharmaceutically acceptable salt thereof.

6. A compound as claimed in claim 1 which is (S)-2-methyl-1-phenyl-2-(pyridin-2-yl)propan-1-amine or a hydrochloric, hydrobromic, sulfuric, phosphoric, citric, tartaric, lactic, pyruvic, acetic, succinic, fumaric, maleic, methanesulphonic or benzenesulphonic acid salt thereof.

7. A compound as claimed in claim 1 which is (S)-2-methyl-1-phenyl-2-(pyridin-2-yl)propan-1-amine fumarate.

8. A compound as claimed in claim 1 which is (S)-2-methyl-1-phenyl-2-(pyridin-2-yl)propan-1-amine.

9. A pharmaceutical composition comprising 2-methyl-1-phenyl-2-(pyridin-2-yl)propan-1-amine or a pharmaceutically acceptable salt thereof and a pharmaceutically acceptable adjuvant, carrier, or diluent.

10. A pharmaceutical composition as claimed in claim 9 comprising (S)-2-methyl-1-phenyl-2-(pyridin-2-yl)propan-1-amine or a pharmaceutically acceptable salt thereof and a pharmaceutically acceptable adjuvant, carrier, or diluent.

11. A pharmaceutical composition as claimed in claim 9 comprising 2-methyl-1-phenyl-2-(pyridin-2-yl)propan-1-amine fumarate or a pharmaceutically acceptable salt thereof and a pharmaceutically acceptable adjuvant, carrier, or diluent.

12. A pharmaceutical composition as claimed in claim 9 comprising (S)-2-methyl-1-phenyl-2-(pyridin-2-yl)propan-1-amine fumarate or a pharmaceutically acceptable salt thereof and a pharmaceutically acceptable adjuvant, carrier, or diluent.

* * * * *